US009782070B2

(12) United States Patent
Utsunomiya et al.

(10) Patent No.: US 9,782,070 B2
(45) Date of Patent: Oct. 10, 2017

(54) FUNDUS PHOTOGRAPHING APPARATUS

(71) Applicant: Kabushiki Kaisha TOPCON, Tokyo (JP)

(72) Inventors: Atsushi Utsunomiya, Tokyo (JP); Hirotake Maruyama, Tokyo (JP); Tomoyoshi Abe, Tokyo (JP); Yasufumi Fukuma, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 197 days.

(21) Appl. No.: 14/889,775

(22) PCT Filed: Apr. 4, 2014

(86) PCT No.: PCT/JP2014/059945
§ 371 (c)(1),
(2) Date: Nov. 6, 2015

(87) PCT Pub. No.: WO2014/185188
PCT Pub. Date: Nov. 20, 2014

(65) Prior Publication Data
US 2016/0113488 A1    Apr. 28, 2016

(30) Foreign Application Priority Data
May 15, 2013  (JP) ................................ 2013-102801

(51) Int. Cl.
*A61B 3/14*    (2006.01)
*A61B 3/12*    (2006.01)
(Continued)

(52) U.S. Cl.
CPC .......... *A61B 3/1208* (2013.01); *A61B 3/1025* (2013.01); *A61B 3/14* (2013.01); *G02B 26/0833* (2013.01); *G02B 26/101* (2013.01)

(58) Field of Classification Search
CPC ....... A61B 3/1025; A61B 3/12; A61B 3/1208; A61B 3/1225
(Continued)

(56) References Cited

U.S. PATENT DOCUMENTS 8,277,047 B2   10/2012   Koschmieder
8,279,509 B2   10/2012   Maruyama et al.
(Continued)

FOREIGN PATENT DOCUMENTS

AT    304316 T    9/2005
AT    486520 T    11/2010
(Continued)

OTHER PUBLICATIONS

International Search Report issued in PCT/JP2014/059945, dated Apr. 28, 2014.

*Primary Examiner* — Huy K Mai
(74) *Attorney, Agent, or Firm* — Studebaker & Brackett PC

(57) ABSTRACT

The fundus photographing apparatus of the present invention includes an illumination light source that generates illumination light flux for illuminating a fundus (of a subject eye), a scanning optical system that converts the illumination light flux from the illumination light source unit into spot light to scan the fundus in two-dimensional directions of a horizontal direction and a vertical direction by the spot light, a light receiver that receives reflected light from each portion of the fundus illuminated by the spot light, and a fundus image acquiring unit that acquires a fundus image based on a signal from the light receiver, wherein the scanning optical system is provided with a scanner including a reflection mirror plate that rotates about orthogonal two axes to simultaneously deflect the spot light in the vertical direction and the horizontal direction for scanning.

12 Claims, 9 Drawing Sheets

(51) Int. Cl.
*A61B 3/10* (2006.01)
*G02B 26/10* (2006.01)
*G02B 26/08* (2006.01)

(58) Field of Classification Search
USPC .................................. 351/205, 206, 218
See application file for complete search history.

(56) References Cited

U.S. PATENT DOCUMENTS

| | | | |
|---|---|---|---|
| 2004/0116811 A1 | 6/2004 | Koschmieder | |
| 2007/0081166 A1 | 4/2007 | Brown et al. | |
| 2009/0244668 A1 | 10/2009 | Fujino et al. | |
| 2010/0103492 A1 | 4/2010 | Maruyama et al. | |
| 2012/0101373 A1 | 4/2012 | Buckland et al. | |
| 2012/0203086 A1 | 8/2012 | Rorabaugh et al. | |
| 2012/0218613 A1 | 8/2012 | Maruyama et al. | |
| 2013/0053700 A1 | 2/2013 | Ignotz et al. | |
| 2013/0120710 A1* | 5/2013 | Buckland | A61B 3/1005 351/206 |
| 2013/0128225 A1 | 5/2013 | Wall et al. | |
| 2013/0135583 A1 | 5/2013 | Gray et al. | |
| 2013/0215385 A1* | 8/2013 | Hirose | A61B 3/14 351/206 |

FOREIGN PATENT DOCUMENTS

| | | |
|---|---|---|
| AU | 2011273205 A1 | 1/2013 |
| AU | 2011273206 A1 | 1/2013 |
| CA | 2 802 786 A1 | 1/2012 |
| CA | 2 802 829 A1 | 1/2012 |
| CN | 102958424 A | 3/2013 |
| CN | 102984995 A | 3/2013 |
| DE | 10155464 A1 | 5/2003 |
| EP | 1 443 853 A1 | 8/2004 |
| EP | 1 443 853 B1 | 9/2005 |
| EP | 1 928 297 A1 | 6/2008 |
| EP | 2 587 984 A2 | 5/2013 |
| EP | 2 587 985 A1 | 5/2013 |
| EP | 2 635 186 A2 | 9/2013 |
| EP | 2 635 187 A2 | 9/2013 |
| GB | 1011095.5 | 7/2010 |
| GB | 1011096.3 | 7/2010 |
| GB | 1100555.0 | 1/2011 |
| JP | 2005-508689 A | 4/2005 |
| JP | 2009-510445 A | 3/2009 |
| JP | 2009-119153 A | 6/2009 |
| JP | 2009-265608 A | 11/2009 |
| JP | 2010-107628 A | 5/2010 |
| JP | 4774261 B2 | 9/2011 |
| JP | 2012-185418 A | 9/2012 |
| JP | 2013-000825 A | 1/2013 |
| JP | 2013-029849 A | 2/2013 |
| JP | 2013-056171 A | 3/2013 |
| JP | 2013-532039 A | 8/2013 |
| WO | 03/041573 A1 | 5/2003 |
| WO | 2007/041125 A1 | 4/2007 |
| WO | 2012/001381 A2 | 1/2012 |
| WO | 2012/001382 A1 | 1/2012 |
| WO | 2012/061835 A2 | 5/2012 |
| WO | 2012/095620 A1 | 7/2012 |

* cited by examiner

FUNDUS PHOTOGRAPHING APPARATUS

CROSS-REFERENCE TO RELATED APPLICATION

The present application is based on and claims priority from Japanese Patent Application No. 2013-102801, filed on May 15, 2013, the disclosure of which is hereby incorporated by reference in its entirety.

TECHNICAL FIELD

This invention is related to improvement in a fundus photographing apparatus that two-dimensionally scans a fundus with spot light to acquire a fundus image by receiving the spot light reflected by the fundus.

BACKGROUND ART

Conventionally, a fundus photographing apparatus has been known. The conventional apparatus is configured to two-dimensionally scan a fundus with spot light in the horizontal and vertical directions to acquire a fundus image by receiving the spot light reflected by the fundus.

This fundus photographing apparatus includes a scanning optical system having a horizontal direction scanning optical system and a vertical direction scanning optical system. The horizontal direction scanning optical system is provided with a polygon mirror while the vertical direction scanning optical system is provided with a Galvano mirror (refer to Patent Literature 1).

The fundus photographing apparatus is configured to scan the fundus at high speed with the polygon mirror. Such high speed scanning makes it possible for the apparatus to obtain sufficient information of the reflected light from the fundus for acquiring the fundus image, and to improve resolution of the fundus image.

CITATION LIST

Patent Literature

Patent Literature 1: Japanese Patent No. 4774261

SUMMARY

Technical Problem

A portable fundus photographing apparatus has been requested in recent years to facilitate mass scanning and self-examination, for example.

However, in the conventional fundus photographing apparatus, it is difficult to downsize the scanning optical system since the scanning optical system is provided with the polygon mirror. The scanning optical system is also provided with a driver for the polygon mirror (for example, spindle motor), which inevitably increases the weight of the scanning optical system.

The present invention has been made in view of the above circumferences. An object of the present invention is to provide a downsized and lightweight fundus photographing apparatus that can scan a fundus at high speed.

Solution to Problem

A fundus photographing apparatus according to the present invention includes an illumination light source unit that generates illumination light flux for illuminating a fundus of a subject eye, a scanning optical system that converts the illumination light flux from the illumination light source unit into spot light to scan the fundus in two-dimensional directions of a horizontal direction and a vertical direction by the spot light, a light receiver that receives reflected light from each portion of the fundus illuminated by the spot light, and a fundus image acquiring unit that acquires a fundus image based on a signal from the light receiver, wherein the scanning optical system is provided with a scanner including a reflection mirror plate that rotates about orthogonal two axes to simultaneously deflect the spot light in the vertical direction and the horizontal direction for scanning.

Advantageous Effects

According to the present invention, since the scanning optical system is provided with the scanner having the reflection mirror plate capable of rotating about two axes, the downsized and lightweight fundus photographing apparatus capable scanning the fundus at high speed can be achieved.

DESCRIPTION OF EMBODIMENT

Hereinafter, an embodiment of a fundus photographing apparatus according to the present invention will be described with reference to the drawings.

(Overview of External Appearance Configuration of Fundus Photographing Apparatus)

Figure 1:
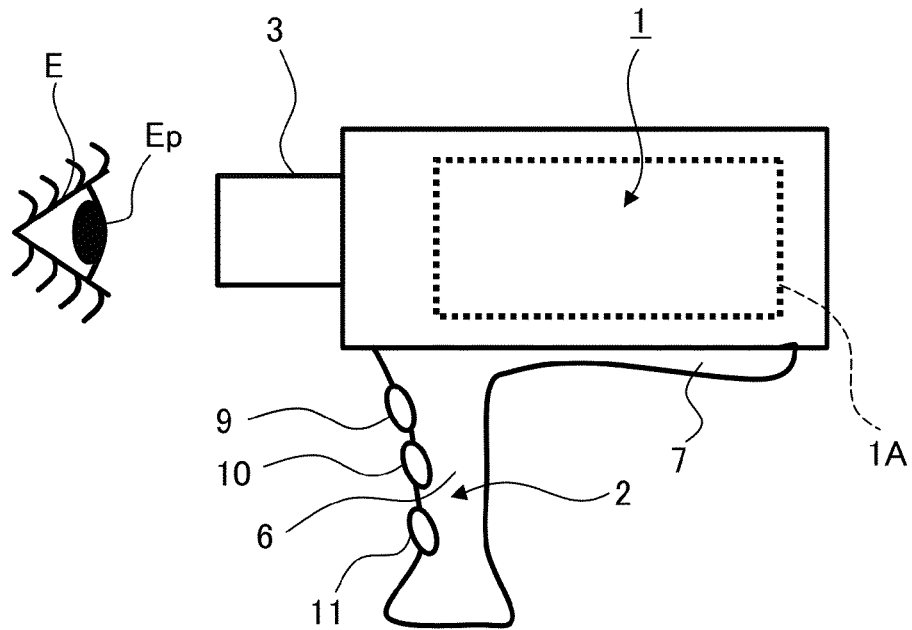
FIG. 1 is a side view showing a portable fundus photographing apparatus as one example of a fundus photographing apparatus according to an embodiment of the present invention.

FIGS. 1 to 4 are views showing a portable fundus photographing apparatus according to the present invention. In FIG. 1, reference number 1 denotes a fundus photographing apparatus body as a case and reference number 2 denotes a handle.

Figure 2:
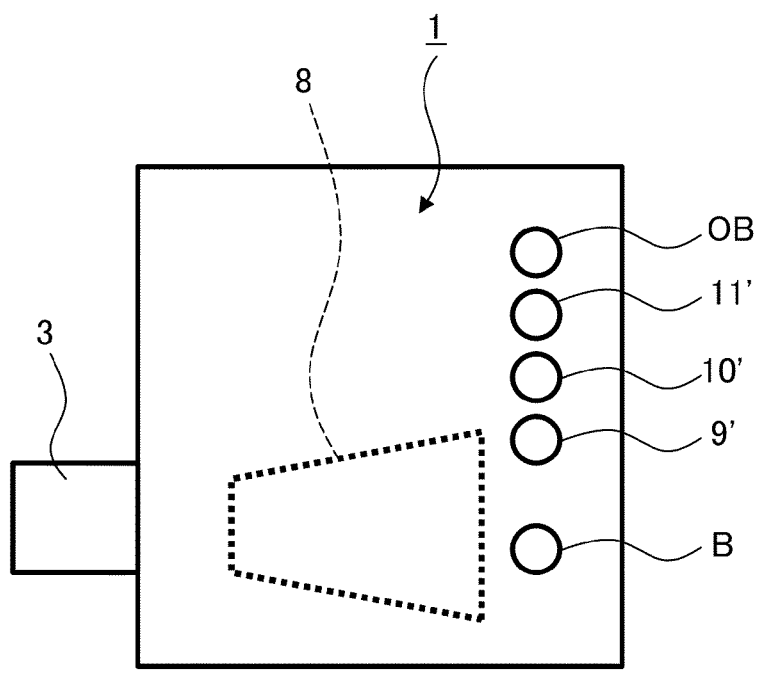
FIG. 2 is a top view showing the portable fundus photographing apparatus illustrated in FIG. 1.
Figure 3:
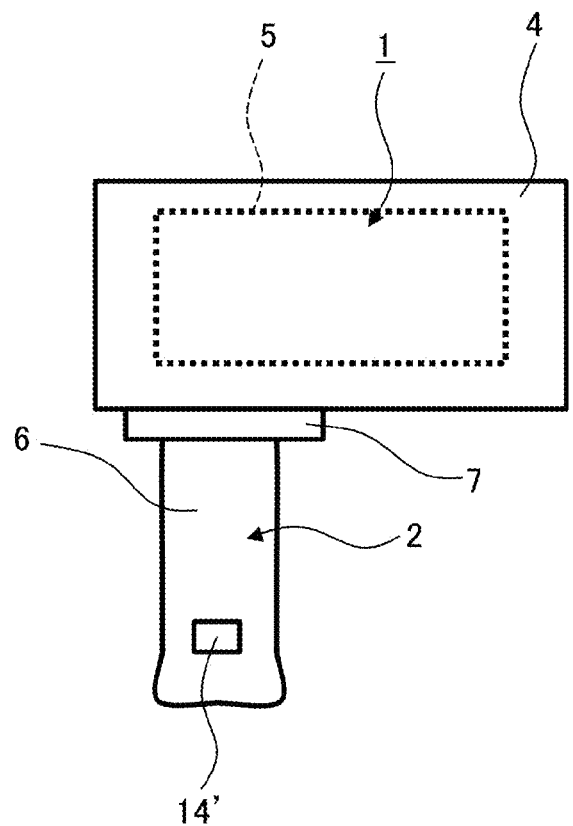
FIG. 3 is a back view showing the portable fundus photographing apparatus illustrated in FIG. 1, as seen from an examiner side.

As illustrated in FIGS. 1 and 2, an eyepiece tube 3 is provided on the front side of the fundus photographing apparatus body 1 (the side facing a subject). As illustrated in FIG. 3, a transparent plate 4 is provided on the back side of the fundus photographing apparatus body 1 (the side facing an examiner).

A liquid crystal display screen 5 of a monitor can be viewed through the transparent plate 4. The fundus photographing apparatus body 1 is provided therein with a scanning optical system as an observation photographing optical system, a control circuit for controlling the scanning optical system, a fundus image acquiring unit, a lighting control circuit, a light receiver, a monitor, a power supply circuit, and other driving mechanisms required for fundus observation and photographing.

As illustrated in FIG. 2, a power button B for power on/off is provided on the top face of the fundus photographing apparatus body 1. As illustrated in FIG. 2, the eyepiece tube 3 is provided on the left side of the fundus photographing apparatus body 1 as viewed from the examiner side.

The handle 2 is provided with a grip 6 and a detachable protrusion 7. A trapezoidal recess 8 illustrated by the dotted line in FIG. 2 is provided in the bottom face of the fundus photographing apparatus body 1 in the position corresponding to the position of the eyepiece tube 3.

The detachable protrusion 7 has a shape corresponding to the shape of the recess 8, and is fitted in the recess 8. A magnet member (not shown) is attached to one of the detachable protrusion 7 and the recess 8.

A magnet that is attracted to the magnet member is attached to the other of the detachable protrusion 7 and the recess 8. In this embodiment, the handle 2 is detachably fixed to the fundus photographing apparatus body 1 by the attractive force of the magnet member; however, this is not limited thereto.

Figure 4:
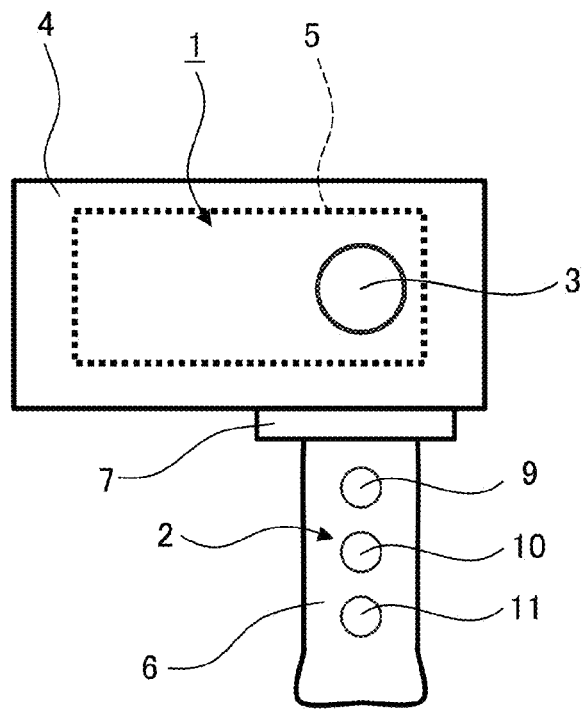
FIG. 4 is a front view showing the portable fundus photographing apparatus illustrated in FIG. 1, as seen from a subject side.
Figure 5:
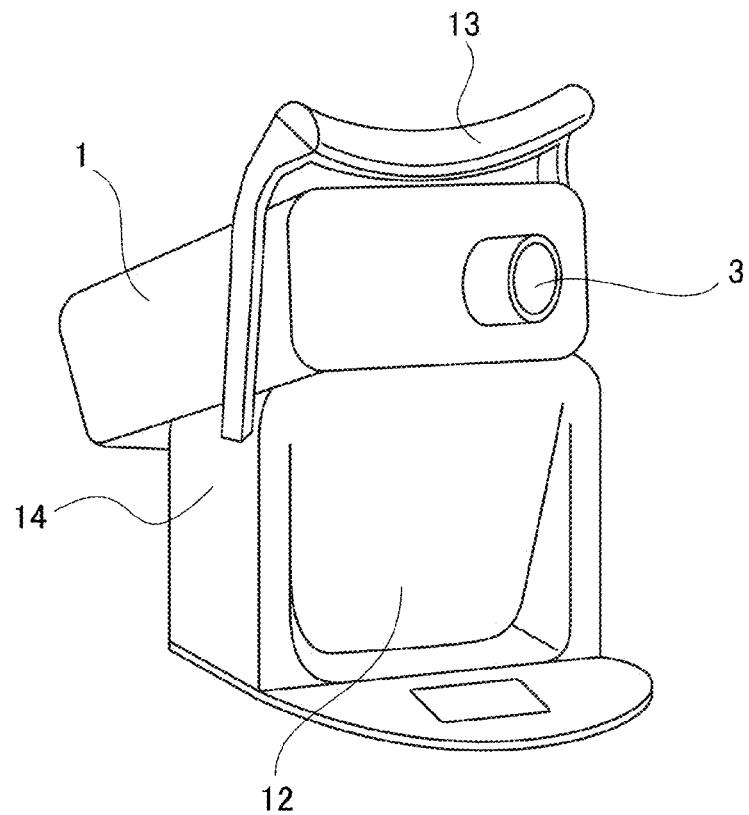
FIG. 5 is an external appearance view showing a support detachably supporting the fundus photographing apparatus illustrated in FIG. 1.

As illustrated in FIG. 4, the grip 6 of the handle 2 is provided with a photographing button 9, alignment button 10, and focus button 11 that make handheld photographing possible. The functions of these buttons are described later. As illustrated in FIG. 5, the fundus photographing apparatus of this embodiment can be used in a state of being mounted on a support 12.

The alignment button 10 is used for aligning an optical axis of a later-described objective lens with a visual axis of a subject eye E; however, the detailed description thereof is omitted. The focus button 11 is used for focusing spot light on a fundus Er of the subject eye E by the objective lens. The photographing button 9 is used for photographing the fundus Er.

A forehead pad 13 is provided on the upper part of the support 12. An engaging protrusion (not shown) is formed in an inclined portion 14 of the support 12. When the engaging protrusion is fitted in the recess 8, the fundus photographing apparatus body 1 is fixed to the support 12.

As illustrated in FIG. 2, a photographing button 9', alignment button 10', and focus button 11' are provided on the top face of the fundus photographing apparatus body 1. Operations of these buttons are effective when the fundus photographing apparatus body 1 is mounted on the support 12. The photographing button 9', alignment button 10', and focus button 11' are enabled/disabled via, for example, a detection switch (not shown) provided on the support 12.

Note that the photographing button 9', alignment button 10', and focus button 11' can be enabled even when the fundus photographing apparatus body 1 with the handle 2 being detached is used without being mounted on the support 12.

Figure 6:
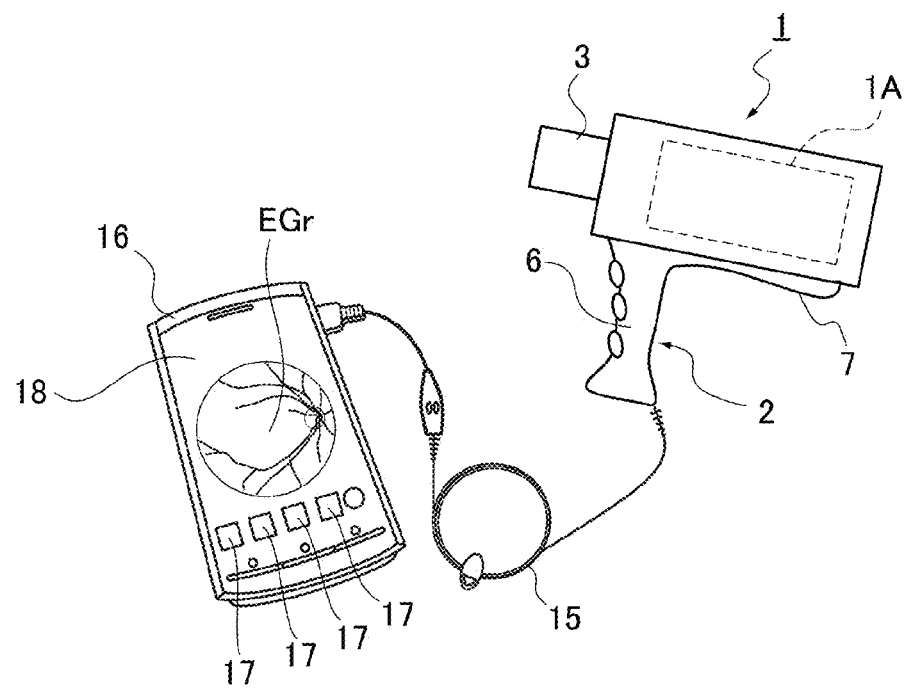
FIG. 6 is a view showing the funds photographing apparatus illustrated in FIG. 1 that is connected to a portable information device via a cord.

As illustrated in FIG. 3, an attachment plug 14' is provided in the lower part of the grip 6 for connecting a portable information device 16 such as a smartphone, tablet computer, and personal digital assistant (PDA). The attachment plug 14' is connected to the portable information device 16 illustrated in FIG. 6 via a cord 15.

The portable information device 16 is provided with a plurality of operation buttons 17. These operation buttons 17 are used as alternatives to the photographing button 9, alignment button 10, and focusing button 11.

In this embodiment, a fundus image EGr is displayed on the display screen 18 of the portable information device 16. However, such a configuration is not limited thereto. The fundus image EGr may be stored in a later-described built-in memory, and output by an output button OB illustrated in FIG. 2.

In the following, a description is given to an illumination light source unit, the scanning optical system, control circuit, lighting control circuit, light receiver, fundus image acquiring unit, and power circuit of the portable fundus photographing apparatus. However, the present invention can be applicable to a fundus photographing apparatus that can be used as a portable apparatus as well as a stationary apparatus and a stationary fundus photographing apparatus.

In this embodiment, the fundus image EGr is sequentially stored in the built-in memory. However, the fundus image EGr may be sent to a medical institution via a wired telephone line or a wireless telephone line.

(Overview of Optical System)

Figure 7:
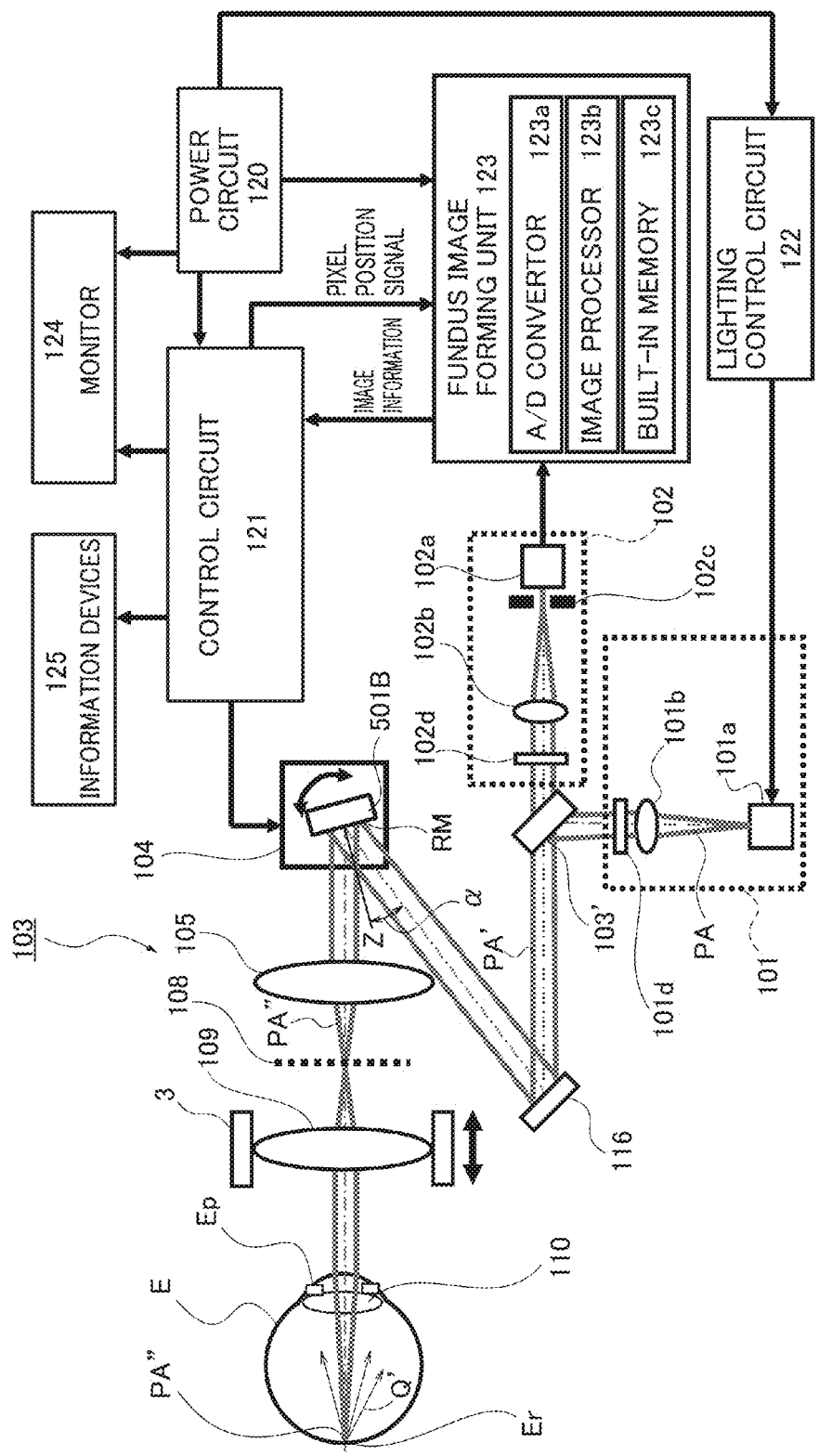
FIG. 7 is a block diagram showing a scanning optical system and a control circuit of the fundus photographing apparatus according to the embodiment of the present invention.

FIG. 7 is a block diagram showing the illumination light source unit, scanning optical system, control circuit, lighting control circuit, light receiver, fundus image acquiring unit, and power circuit of the fundus photographing apparatus. In FIG. 7, reference number 101 denotes the illumination light source unit, 102 denotes the light receiver, 103 denotes the scanning optical system, 121 denotes the control circuit, 120 denotes the power circuit, 122 denotes the lighting control circuit, 124 denotes the monitor, and 125 denotes various information devices.

The illumination light source unit 101 includes an illumination light source 101a. A light source having a high spatial coherence is used for the illumination light source 101a. Such a light source includes, for example, a semiconductor laser (swept laser and super luminescence diode), solid-state laser, gas laser, and fiber laser in which these lasers are optically coupled to optical fibers.

The illumination light source unit 101 is provided with a collimator lens 101b and an optical element 101d. The collimator lens 101b converts illumination light flux PA from the illumination light source 101a into parallel light flux PA'.

The optical element 101d is provided as appropriate, and includes a light flux control element having an opening and a wavelength control element such as a wavelength plate, polarizer, and wavelength selection filter, or a complex element in which these elements are combined.

The scanning optical system 103 includes a beam splitter 103', fixed mirror 116, scanner 104, relay lens 105, objective lens 109, and the eyepiece tube 3. The illumination light flux PA converted into the parallel light flux PA' by the collimator lens 101b is guided to the beam splitter 103'.

The beam splitter 103' includes a half mirror, dichroic mirror, and light beam splitter. The parallel light flux PA' guided to the beam splitter 103' is guided to the scanner 104 via the fixed mirror 116.

The scanner 104 includes a reflection mirror capable of rotating about two axes orthogonal to each other to deflect light for scanning the fundus Er of the subject eye E in the vertical and horizontal directions. The details of the scanner 104 are described later.

The parallel light flux PA' reflected by the scanner 104 is guided to the relay lens 105. The relay lens 105 converts the parallel light flux PA' into spot light PA" to be imaged in the air on a plane 108 conjugate to the fundus Er.

The spot light PA" is guided to the objective lens 109 as a focus lens. The objective lens 109 is held in the eyepiece tube 3. The objective lens 109 is disposed to face the subject eye E, and moves back and forth in the optical axis direction according to refractive power of the subject eye E.

The spot light PA" passed through the objective lens 109 is reconverted into the parallel light flux. The parallel light flux passes through a pupil Ep of the subject eye E, and enters the subject eye E. When the conjugate plane 108 coincides with the fundus Er of the subject eye E by moving the objective lens 109 in the optical axis direction, the clear spot light PA" is imaged on each portion of the fundus Er.

Figure 8:
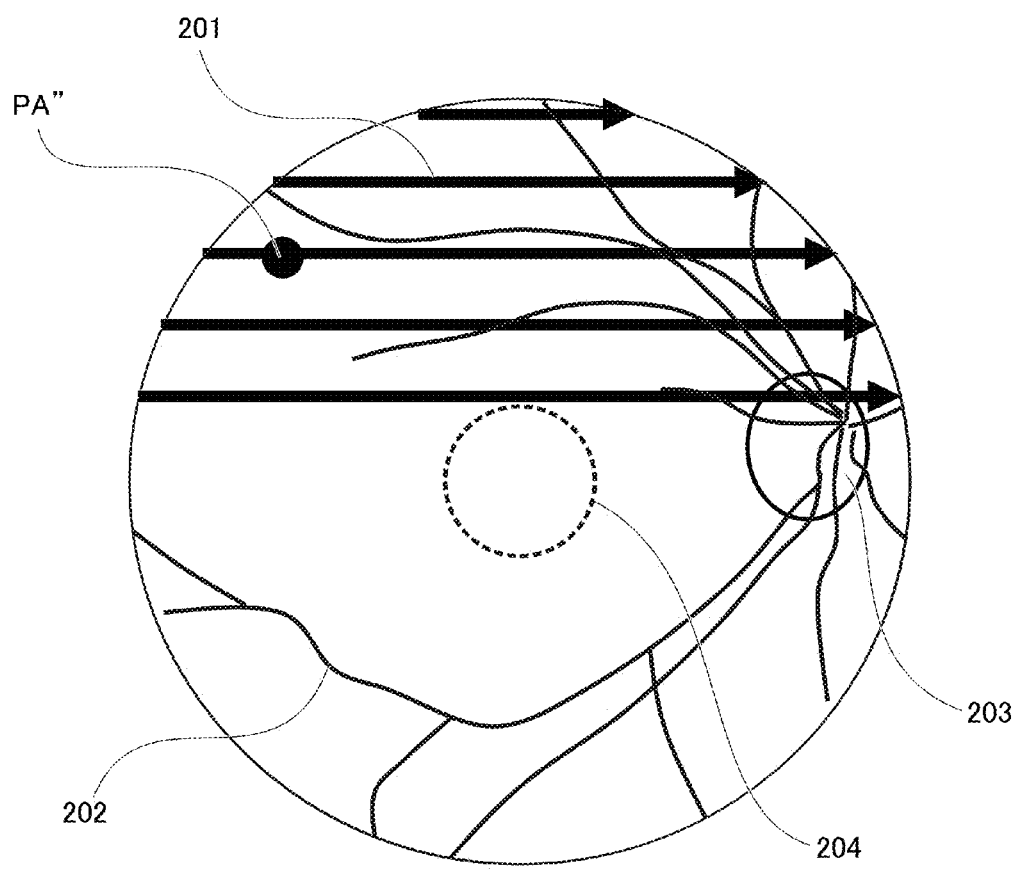
FIG. 8 is a view explaining a scanning state of a fundus.

As illustrated in FIG. 8, after the fundus Er is scanned in the horizontal direction by the spot light PA", the fundus Er is sequentially scanned in the vertical direction by the spot light PA" while deflecting the light in the horizontal direction and the vertical direction with the scanner 104. In FIG. 8, reference number 201 denotes a scanning trajectory in the horizontal direction by the spot light PA", 202 denotes a blood vessel, 203 denotes a papilla portion, and 204 denotes a macula portion. Namely, the fundus Er is simultaneously scanned in the two-dimensional directions with the scanner 104.

In this embodiment, in order to acquire the fundus image, the scanning trajectory 201 of the spot light PA" is drawn by scanning the fundus Er in parallel in the horizontal direction. However, various figures such as an arc shape, polygon shape, and star shape can be drawn on the fundus Er by controlling the control circuit 121.

Reflected light Q' of the spot light PA" reflected by each portion of the fundus Er is guided to the objective lens 109 via a crystal lens 110 and the pupil Ep as illustrated in FIG. 7, and is condensed by the objective lens 109. After the reflected light Q' condensed by the objective lens 109 is imaged in the air on the conjugate plane 108, the reflected light Q' is guided to the beam splitter 103' via the relay lens 105, scanner 104, and fixed mirror 116, and is then guided to the light receiver 102 via the beam splitter 103'.

The light receiver 102 includes a light receiving element 102a, light flux control element 102c, condensing lens 102b, and optical element 102d. The light receiving element 102a is provided in a focus position of the condensing lens 102b. The light flux control element 102c includes an aperture member having a circular opening, ellipse opening, or toroidal opening.

The optical element 102d is provided as appropriate. The optical element 102d includes a light flux control element having an opening, a wavelength control element such as a wavelength plate, polarizer, and wavelength selection filter, or a complex element in which the these elements are combined.

In FIG. 7, for the purpose of simplifying the description, the illumination light source unit 101 generates single color illumination light. However, for the purpose of generating a color image, an illumination light source for generating light of each color of R, G, and B and infrared light may be provided in the illumination light source unit 101, a dichroic mirror for synthesizing light having different wavelengths may be provided, and the light is guided to the beam splitter 103' after being synthesized.

For the purpose of dissolving the reflected light in which a plurality of wavelengths are mixed to be received, a dichroic mirror for dissolving an optical path may also be provided in the light receiver 102, and an light-receiving element may be provided for each wavelength to receive the reflected light Q' for each wavelength.

The control circuit 121 controls the scanner 104 and also the fundus image acquiring unit 123. The lighting control circuit 122 controls the lighting of the illumination light source unit 101. The power circuit 120 supplies power to the control circuit 121, fundus image acquiring unit 123, lighting control circuit 122, and monitor 124.

The fundus image acquiring unit 123 includes an A/D convertor 123a, image processor 123b, and built-in memory 123c. A pixel position signal and a light-receiving signal are input in the fundus image acquiring unit 123. The fundus image acquiring unit 123 creates the image information based on the pixel position signal and the light-receiving signal. The image information is output to the control circuit 121. The control circuit 121 controls the scanning of the scanner 104. The details are described later.

The image information is sent to the monitor 124 as appropriate, and is displayed on the liquid crystal display screen 5. The image information is also sent to the information device 125 as appropriate. The image information includes photographing dates, names of subjects, and disease names.

The information device 125 includes a portable information device 16 such as a personal computer, smartphone, tablet computer, and portable digital assistance (PDA). Image information or image evaluation information from an information device different from the information device 125 can be sent to the control circuit 121, and such information can be displayed on the liquid crystal display screen 5 of the monitor 124.

(Configuration of Scanner 104)

Figure 9:
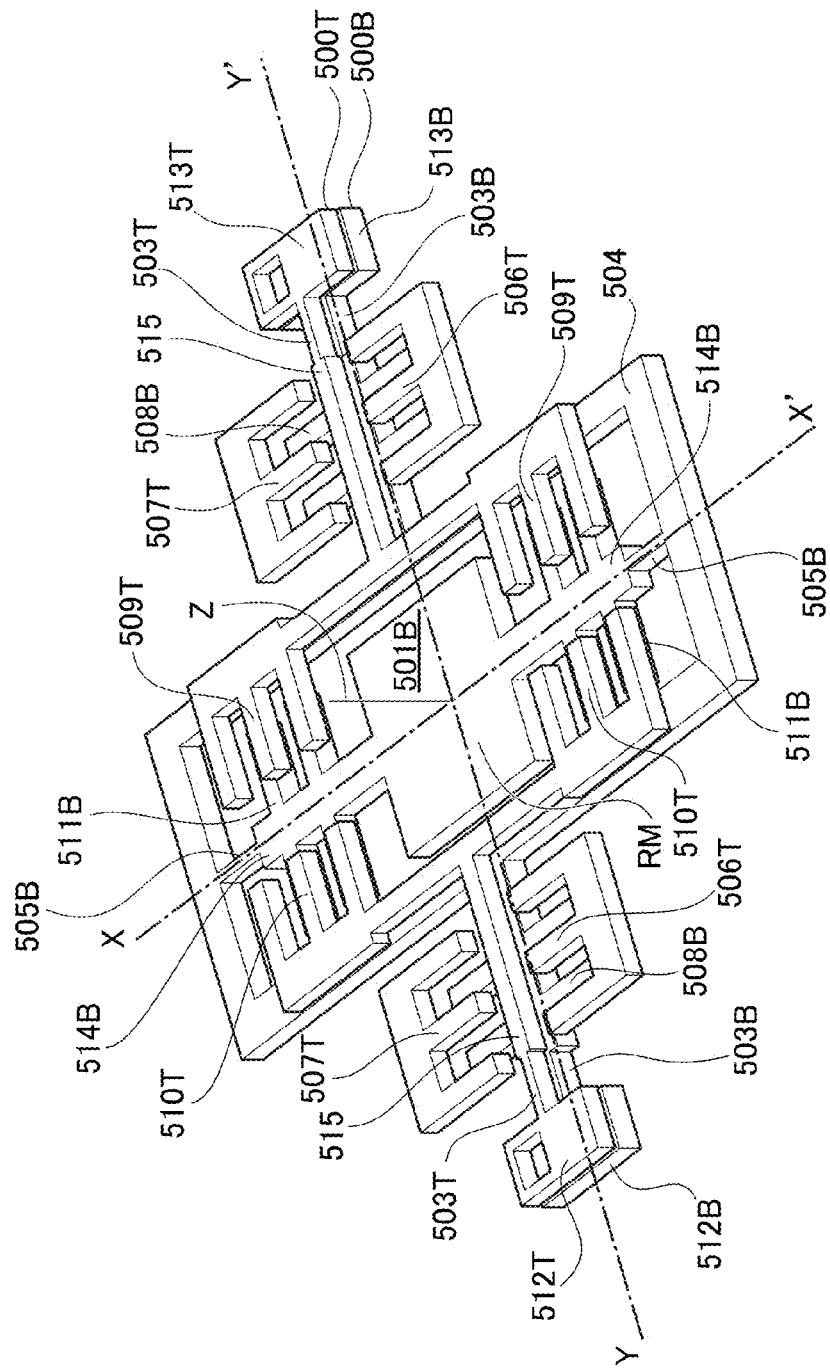
FIG. 9 is a perspective view showing a configuration of a scanner illustrated in FIG.

The scanner 104 includes, for example, a MEMS scanner illustrated in FIG. 9. A method of manufacturing such a MEMS scanner is already known (refer to, Japanese Laid-Open Patent Application Nos. 2010-107628, 2013-000825, 2013-29849, and 2012-185418, and U.S. Pat. No. 8,279,509).

The MEMS scanner includes an upper silicon layer 500T and a lower silicon layer 500B. An electric insulation layer (not shown) made of SiO2 is provided between the upper silicon layer 500T and the lower silicon layer 500B.

The lower silicon layer 500B is mechanically supported by a further lower layer (not shown) in anchor portions 512B and 513B. The MEMS scanner includes a reflection mirror plate 501B. A pair of inside beams 514B is formed in the reflection mirror plate 501B. Each of the inside beams 514B is connected to an inside fixed portion 504 via an inside spring 505B. An inside movable teeth 511B are formed in the inside beam 514B.

The inside movable teeth 511B are disposed to face inside combs 509T and 510T. The inside movable teeth 511B and the inside combs 509T and 510T constitute a part of a pair of inside electrostatic actuators.

These are supported by the inside fixed portion 504. A pair of outside beams 515 is formed in the inside fixed portion 504. A pair of outside beams 515 is connected to anchor portions 512B, 512T, 513B, and 513T via external springs 503B and 503T. An outside movable comb 508B is formed in the outside beam 515.

The outside movable comb 508B is disposed to face outside fixed combs 506T and 507T. The outside movable comb 508B and an outside fixed comb 506T and 507T constitute a part of a pair of outside electrostatic actuators. The outside fixed combs 506T and 507T are mechanically fixed.

The surface of the reflection mirror plate 501B includes a reflection plane RM. The reflection mirror plate 501B rotates about the optical axis of the relay lens 105 at equal angles both in the two-axis directions. Reference number Z denotes a standard normal line of the reflection plane RM when the reflection mirror plate 501B is located in the rotation center. The lower silicon layer 500B is installed in GND, for example. The inside movable comb 511B and the inside combs 509T and 510T are used to rotate the reflection mirror plate 501B about an X-X' axis.

More specifically, the reflection mirror plate 501B rotates about the X-X' axis by applying voltage to a pair of inside combs 509T and 510T via the anchor portions 512T and 513T. The outside movable comb 508B and the outside fixed combs 506T and 507T are also used to rotate the reflection mirror plate 501B about a Y-Y' axis.

More specifically, the reflection mirror plate 501B rotates about the Y-Y' axis orthogonal to the X-X' axis by applying voltage to the outside fixed combs 506T and 507T. A method of driving the MEMS mirror includes a DC driving method that rotates the MEMS mirror from the first angle to the second angle by applying DC voltage and a resonance driving method that swings the MEMS mirror by applying periodic voltage. In the resonance driving method, the rotation angle changes in a sinewave shape. These driving methods are disclosed in Japanese Laid-Open Patent Application No. 2009-265608.

Figure 10:
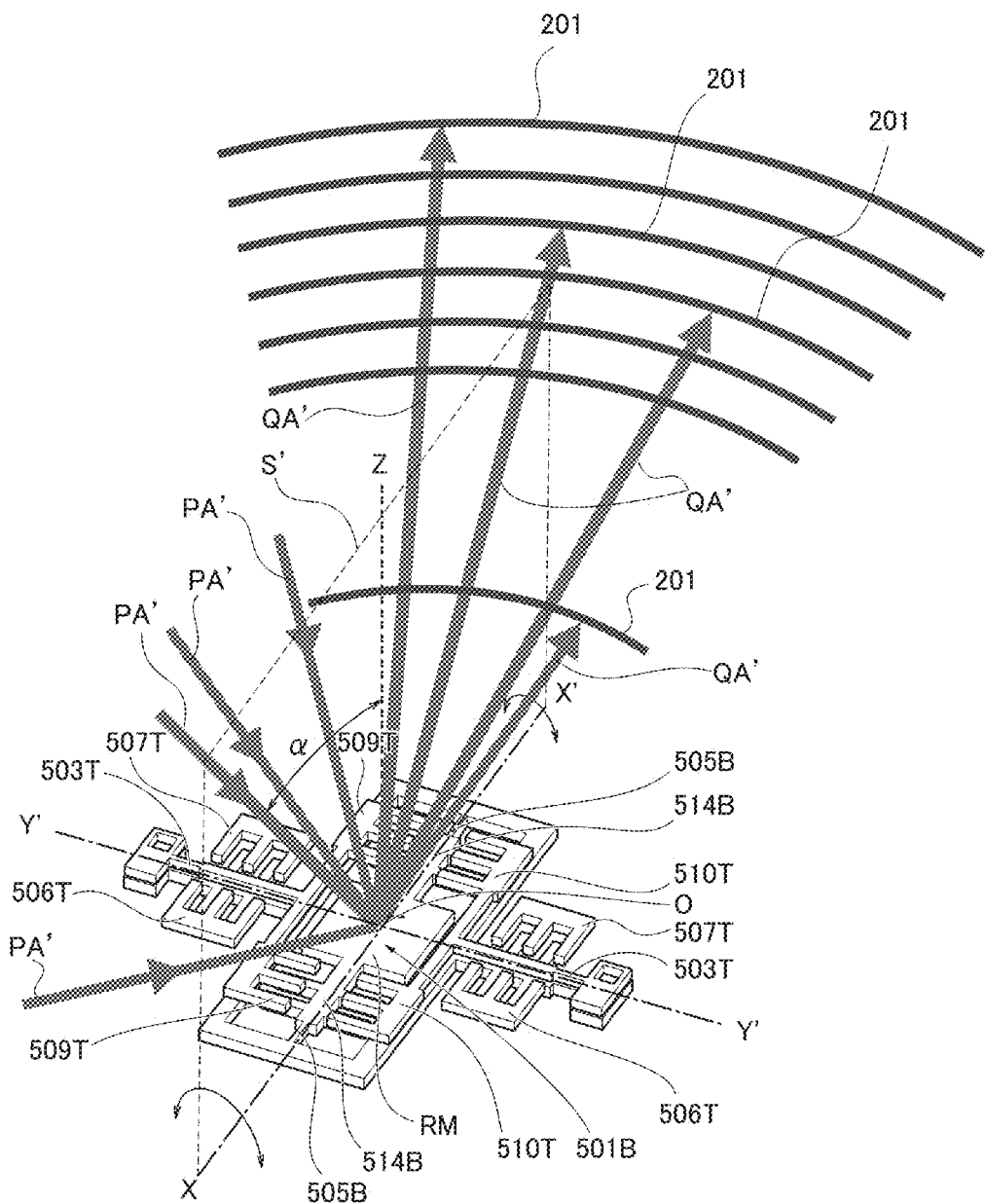
FIG. 10 is a view explaining arc scanning trajectories.

In this embodiment, in order to correct distortion generated when deflecting the parallel light flux PA' in the two-axis directions, an incident angle α relative to the standard normal line Z of the reflection plane RM is set to be smaller than 45° as illustrated in FIG. 10.

FIG. 10 is a view schematically illustrating a relationship among the reflection mirror plate 501B, parallel light flux PA' as incident light flux incident on the reflection mirror plate 501B, and reflected light flux QA' by the reflection plane RM of the reflection mirror plate 501B. In FIG. 10, S' denotes an incident plane containing the incident light flux and the standard normal line Z.

As illustrated in FIG. 10, when the reflection mirror plate 501B rotates about the X-X' axis, the reflection plane RM of the reflection mirror plate 501B rotates about the X-X' axis. The reflected light flux QA' in which the incident light flux from the X-X' axis direction is reflected by the reflection plane RM of the reflection mirror plate 501B is thereby deflected in the direction that the reflection plane RM rotates about the X-X' axis.

As a result, the reflected light flux QA' rotates in the rotation direction of the reflection mirror plate 501B, and the scanning trajectory 201 by the reflected light flux QA' has an arc shape.

The reflected light flux QA' comes closer to the X-X' axis as the incident angle α relative to the standard normal line Z increases (as incident angle α comes close to 90°), so that the arc shape has a large curvature. In this case, the X-X' axis direction corresponds to the scanning of the fundus Er in the horizontal direction and the Y-Y' axis direction corresponds to the scanning of the fundus Er in the vertical direction. Here, the reflection mirror plate 501B is tilted relative to the X-X' axis at 2° within the range of ±10° to draw the scanning trajectory 201 in the horizontal direction on the fundus Er, and the reflection mirror plate 501B is tilted relative to the Y-Y' axis at 2° within the range of ±10° to draw the scanning trajectory 201 in the vertical direction on the fundus Er.

Figure 11:
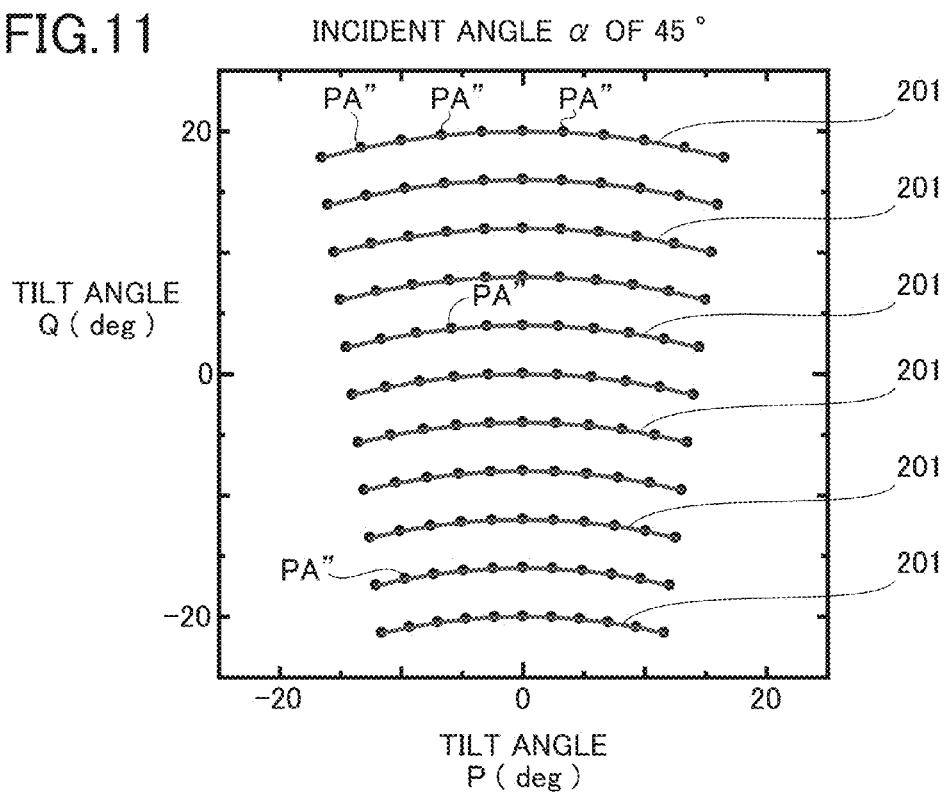
FIG. 11 is a schematic diagram showing scanning trajectories on the fundus obtained by tilting a reflection mirror plate at 2° both in the directions orthogonal to each other with incident light flux (parallel light flux) having an incident angle α of 45°.

FIG. 11 is a pattern diagram illustrating the scanning trajectories 201 drawn on the fundus Er by tilting the reflection mirror plate 501B at 2° both in the X-X' axis direction and the Y-Y' axis direction with the incident light flux (parallel light flux PA') having an incident angle α of 45°. In contrast, FIG. 12 is a pattern diagram illustrating the scanning trajectories 201 drawn on the fundus Er by tilting the reflection mirror plate 501B at 2° both in the X-X' axis direction and the Y-Y' axis direction with the incident light flux having an incident angle α of 20°.

Both of the scanning trajectories 201 with the incident angle α of 45° and the incident angle α of 20° have the arc shape. However, as the incident angle α decreases, the scanning trajectory 201 in the horizontal direction relative to the scanning trajectory 201 in the vertical direction comes close to a straight line, the distortion of the scanning trajectory 201 in the horizontal direction decreases, and the scanning range relative to the fundus Er increases.

Figure 12:
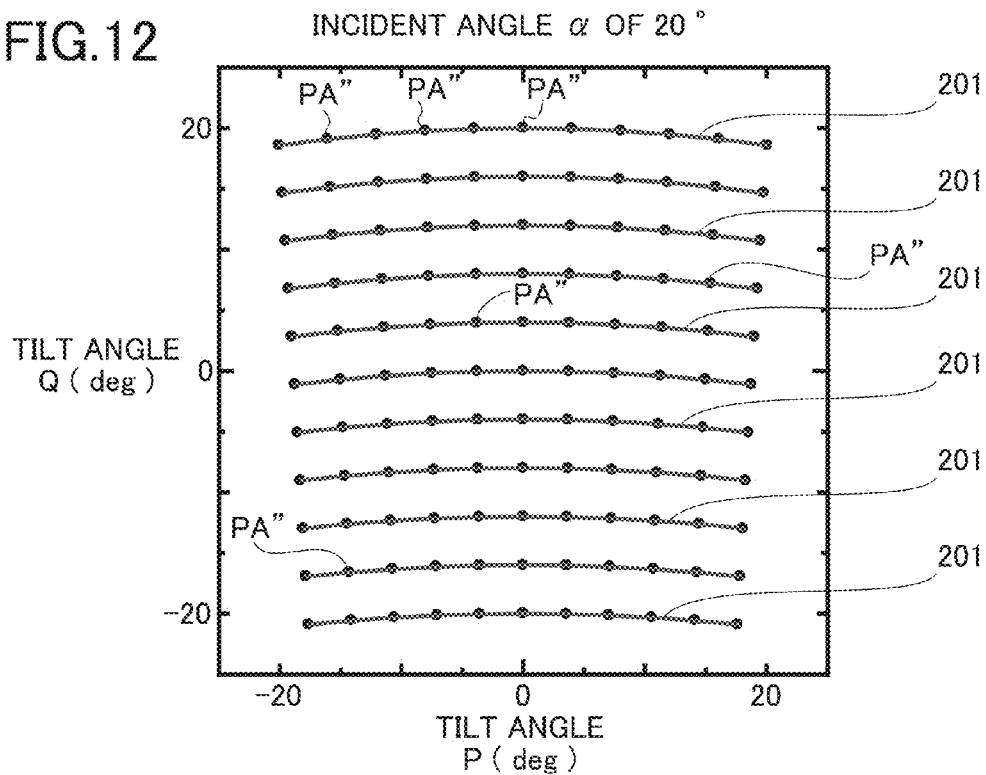
FIG. 12 is a schematic diagram showing scanning trajectories on the fundus obtained by tilting the reflection mirror plate at 2° both in the directions orthogonal to each other with incident light flux (parallel light flux) having an incident angle α of 20°.

In addition, in FIGS. 11 and 12, the horizontal axis represents a tilt angle P relative to the X-X' axis (horizontal axis) and the vertical axis represents a tilt angle Q relative to the Y-Y' axis (vertical axis). Next, a relationship between the size of the reflection mirror plate 501B and the incident angle α of the incident light flux (parallel light flux PA') is described with reference to FIG. 13.

$Mx > D/\cos(\alpha+\beta/2)$ is established where Mx represents the length of the reflection mirror plate 501B in the X-X' axis direction, D represents a width of the incident light flux (parallel light flux PA'), and β represents the maximum scanning angle range (twice the maximum tilt angle of the reflection mirror plate 501B).

When the length Mx does not satisfy the above condition, the circumference light flux of the incident light flux (parallel light flux PA') is not reflected by the reflection plane RM of the reflection mirror plate 501B, resulting in a decrease in the light volume of the reflected light flux QA'. Namely, the light volume of the spot light PA" focused on the fundus Er decreases.

When the width D of the incident light flux (parallel light flux PA') is 1 mm, the incident angle α is 45°, and the maximum scanning angle range β is 20°, it is necessary for the length Mx to be 1.74 mm or more. However, when the incident angle α is changed to 20° while maintaining the width D of the incident light flux (parallel light flux PA') in 1 mm and the maximum scanning angle range β in 20°, the length Mx can be reduced to 1.15 mm or more, which is 0.66 times the length when the incident angle α is 45°. The reflection mirror plate 501B can be therefore downsized.

Figure 13:
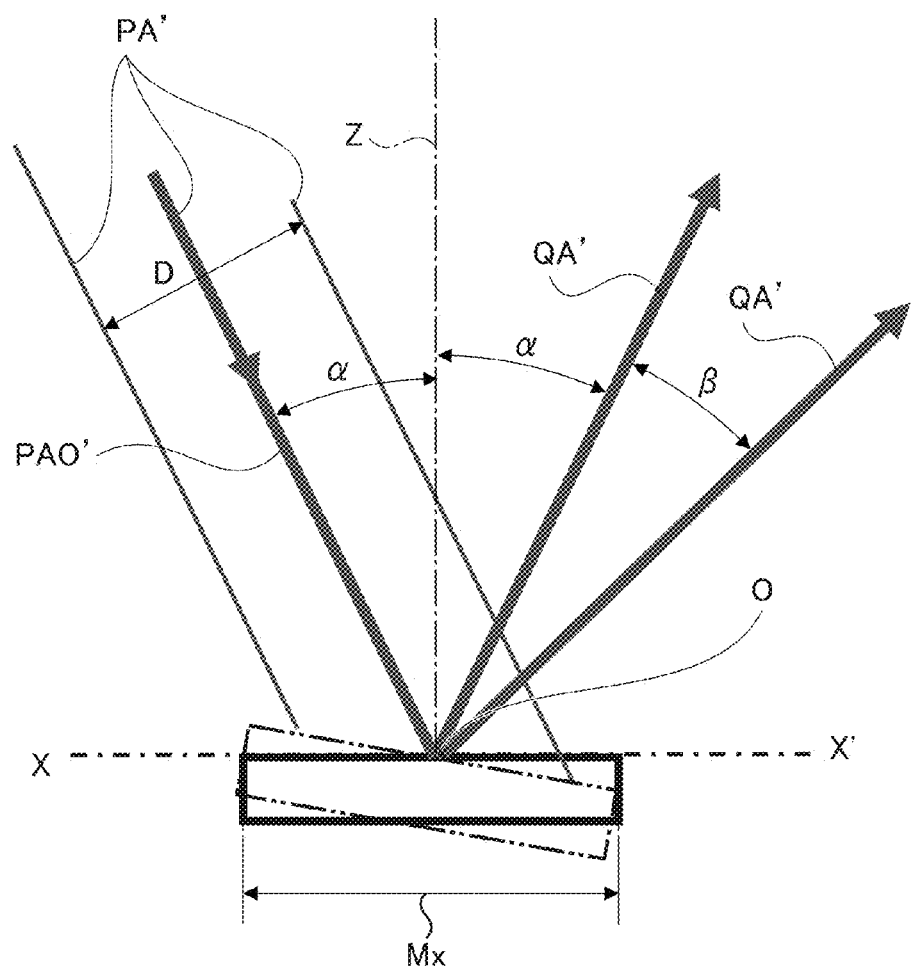
FIG. 13 is a view illustrating a relationship among a size of the reflection mirror plate, incident light flux (parallel light flux), and incident angles.

In FIG. 13, PAO' denotes central light flux incident on the reflection plane RM, and O denotes an intersection point between the standard normal line Z and the central light flux PAO' on the reflection plane RM. When the size is converted into an inertia moment of a mirror plate of the reflection mirror plate 501B, the inertia moment when the incident angle α is 20° becomes 0.29 times the inertia moment when the incident angle α is 45°. Since the inertia moment relative to the rotation of the reflection mirror plate 501B is roughly determined by the mirror plate, the resonance frequency when the incident angle α is 20° reaches about 1.85 times the resonance frequency when the incident angle α is 45° with a fixed spring constant. As a result, high speed response of the apparatus can be improved.

More specifically, when the incident angle α of the reflection mirror plate 501B is set to smaller than 45°, the distortion of the scanning trajectory 201 on the fundus Er can be decreased, and the high speed response of the apparatus can be achieved. A fundus image forming program when acquiring the fundus image EGr can be simplified. With this program, the fundus image EGr is acquired by correcting the distortion of the arc generated when drawing the scanning trajectory 201 on the fundus Er through the scanning with the deflection of the reflection plane RM in the orthogonal two-axis directions.

It is desirable for the incident angle α relative to the reflection plane RM to be within the range of 15° to 30° in view of the relationship between a distortion correcting process when acquiring the fundus image EGr and the scanning angle range β of the reflection mirror plate 501B.

When the incident angle α is excessively increased, the distortion of the scanning trajectory 201 on the fundus Er is excessively increased. For this reason, the distortion when acquiring the fundus image EGr cannot be completely eliminated, and the distortional fundus image EGr may be obtained. Thus, the size of the reflection mirror plate 501B may be increased, and the high speed response of the apparatus may be deteriorated.

On the other hand, when the incident angle α is excessively decreased, the parallel light flux PA' as the scanning light flux may not enter the relay lens 105.

The invention claimed is:

1. A fundus photographing apparatus comprising:
   an illumination light source unit that generates illumination light flux for illuminating a fundus of a subject eye;
   a scanning optical system that converts the illumination light flux from the illumination light source unit into spot light to scan the fundus in two-dimensional directions of a horizontal direction and a vertical direction by the spot light;
   a light receiver that receives reflected light from each portion of the fundus illuminated by the spot light; and
   a fundus image acquiring unit that acquires a fundus image based on a signal from the light receiver, wherein
   the scanning optical system is provided with a scanner including a reflection mirror plate that rotates about orthogonal two axes to simultaneously deflect the spot light in the vertical direction and the horizontal direction for scanning.

2. The fundus photographing apparatus according to claim 1, wherein the scanner is a MEMS scanner.

3. The fundus photographing apparatus according to claim 1, wherein
   the scanning optical system includes an objective lens facing the subject eye and a relay lens that converts the illumination light flux into the spot light to be imaged in an air in a position conjugate to the fundus of the subject eye, the objective lens and the relay lens being provided in an optical path between the subject eye and the scanner, and
   an incident angle of the illumination light flux relative to a standard normal line is smaller than 45°, the standard normal line being a normal line of a reflection plane when the reflection mirror plate is located in a rotation center.

4. The fundus photographing apparatus according to claim 3, wherein the incident angle of the illumination light flux relative to the standard normal line of the reflection plane is within a range of 15° to 30°.

5. The fundus photographing apparatus according to claim 4, wherein the illumination light flux is incident on the reflection mirror plate as parallel light flux, and the relay lens converts the parallel light flux reflected by the reflection mirror plate into the spot light.

6. The fundus photographing apparatus according to claim 3, wherein the illumination light flux is incident on the reflection mirror plate as parallel light flux, and the relay lens converts the parallel light flux reflected by the reflection mirror plate into the spot light.

7. A fundus photographing apparatus comprising:
   an illumination light source unit that generates illumination light flux for illuminating a fundus of a subject eye;
   a scanning optical system that converts the illumination light flux from the illumination light source unit into spot light to scan the fundus in two-dimensional directions of a horizontal direction and a vertical direction by the spot light;
   a light receiver that receives reflected light from each portion of the fundus illuminated by the spot light;
   a fundus image acquiring unit that acquires a fundus image based on a signal from the light receiver;
   a control circuit that controls the scanning optical system and the fundus image acquiring unit;
   a case that incorporates at least a lighting control circuit configured to control lighting of the illumination light source unit; and
   a handle that supports the case, wherein
   the scanning optical system is provided with a scanner including a reflection mirror plate that rotates about orthogonal two axes to simultaneously deflect the spot light in the vertical direction and the horizontal direction for scanning.

8. The fundus photographing apparatus according to claim 7, wherein the scanner is a MEMS scanner.

9. The fundus photographing apparatus according to claim 7, wherein
   the scanning optical system includes an objective lens facing the subject eye and a relay lens that converts the illumination light flux into the spot light to be imaged in an air in a position conjugate to the fundus of the subject eye, the objective lens and the relay lens being provided in an optical path between the subject eye and the scanner, and
   an incident angle of the illumination light flux relative to a standard normal line is smaller than 45°, the standard normal line being a normal line of a reflection plane when the reflection mirror plate is located in a rotation center.

10. The fundus photographing apparatus according to claim 9, wherein the incident angle of the illumination light flux relative to the standard normal line of the reflection plane is within a range of 15° to 30°.

11. The fundus photographing apparatus according to claim 10, wherein the illumination light flux is incident on the reflection mirror plate as parallel light flux, and the relay lens converts the parallel light flux reflected by the reflection mirror plate into the spot light.

12. The fundus photographing apparatus according to claim 9, wherein the illumination light flux is incident on the reflection mirror plate as parallel light flux, and the relay lens converts the parallel light flux reflected by the reflection mirror plate into the spot light.

* * * * *